United States Patent [19]

Lubitzsch et al.

[11] 4,219,038
[45] Aug. 26, 1980

[54] GAS MIXING DEVICE FOR BREATH-PROTECTING, DIVING, MEDICAL AND LABORATORY TECHNIQUES

[75] Inventors: Wolfgang Lubitzsch, Lübeck-Gross Steinrade; Manfred Schinkmann, Lübeck; Holmer Röhling, Reinfeld, all of Fed. Rep. of Germany

[73] Assignee: Drägerwerk Aktiengesellschaft, Fed. Rep. of Germany

[21] Appl. No.: 914,221

[22] Filed: Jun. 9, 1978

Related U.S. Application Data

[63] Continuation of Ser. No. 741,932, Nov. 15, 1976, abandoned.

[30] Foreign Application Priority Data

Nov. 27, 1975 [DE] Fed. Rep. of Germany ....... 2543165

[51] Int. Cl.² ............................................. G05D 11/03
[52] U.S. Cl. ............................................. 137/7; 137/88
[58] Field of Search ..................................... 137/88, 7

[56] References Cited

U.S. PATENT DOCUMENTS

| | | | |
|---|---|---|---|
| 2,072,384 | 3/1937 | Schmidt | 137/88 |
| 2,800,915 | 7/1957 | Tavener | 137/88 |
| 3,298,383 | 1/1967 | Cooper | 137/88 |
| 3,739,799 | 6/1973 | Bickford | 137/88 |
| 3,827,450 | 8/1974 | Leverenz | 137/88 |
| 3,841,344 | 10/1974 | Slack | 137/88 |
| 4,023,587 | 5/1977 | Dobritz | 137/88 |

Primary Examiner—William R. Cline
Assistant Examiner—H. Jay Spiegel
Attorney, Agent, or Firm—McGlew and Tuttle

[57] ABSTRACT

A gas mixing device comprises a plurality of gas lines for the conveyance of the separate gases to be mixed, each of which has a pressure regulator with a pressure control. A common gas mixture line is connected to each of the gas lines downstream of the pressure controls therein and a constant admission pressure regulator is provided in the mixture line. Control pressure is provided from a control pressure source which, for example, may be at the tapping of the gas mixture line. The control pressure is connected to each of the pressure controls for the pressure regulators and the gas lines and this control pressure is regulated by control means which may be in response to the pressure in each of the individual gas lines or in response to the pressure in the common gas mixture line downstream of the constant admission pressure regulator means.

8 Claims, 3 Drawing Figures

GAS MIXING DEVICE FOR BREATH-PROTECTING, DIVING, MEDICAL AND LABORATORY TECHNIQUES

This is a continuation, of application Ser. No. 741,932 filed Nov. 15, 1976 now abandoned.

FIELD AND BACKGROUND OF THE INVENTION

The present invention relates to gas mixing devices and, in particular, to a new and useful gas mixing device for use in breath-protecting, diving, medical and laboratory techniques for preparing gas mixtures having definite mixing ratios, from gas components which are available in pressure vessels or component-conducting lines provided with adjustable pressure regulators and control valves for adjusting the mixing ratio.

DESCRIPTION OF THE PRIOR ART

In gas mixing devices, care must be taken to make certain that the gas mixture ratio, once it is adjusted, remains constant under any operational conditions, including switching of the device on and off since, during the respiration, for example, for narcosis, very small variations in the concentration are of determining importance.

Known mixing devices are based on a method in which two or more pressurized gases are consecutively directed, each through a pressure regulator, into a common mixing tank, with the pressures of the gases to be mixed having the same ratio as the desired volume proportion of the gas components in the gas mixture to be prepared. If, for example, a gas mixture comprises two components with A=70% per volume and B=30% per volume, the pressure in the mixing tank is, first, with the component B brought to P=30 bar and, subsequently, the component A is supplied until the pressure in the tank has increased to 100 bar.

This method has the drawback that mixing inaccuracies occur, inter alia, due to the temperature variations during a rapid filling of the mixing tank, or that the mixing process is not continuous. Difficulties arise with an accurate admixture of small volumes of components and with the attainment of a uniform mixing.

In other mixing devices, two or more gases are directed, each through a choker valve and a flow meter with different pressures, into a common outlet line. The mixing ratio is adjusted with the flow meters. This method has the disadvantage that it necessitates continuous checking of the adjustment of the flow meters and choker valves. Further, an exact predetermined pressure must be continuously ensured in the flow meters or, otherwise, the value indicated at the flow meters would be incorrect.

A further gas mixing method of the prior art employs measuring tanks which are connected to a single or a plurality of common pressure-reducing valves. The measuring tanks are filled with the gases to be mixed. The gases are equally pressurized. The volumina of the mixing tanks are proportional to the composition of the gas mixture to be prepared. If, for example, a measuring tank filled with a gas A and having a volume of 100/1, and a measuring tank with a gas B having a volume of 20/1, both equally pressurized for example to 100 bar are connected to a common pressure-reducing valve, the valve discharges a gas mixture comprising five parts per volume of gas A and one part of gas B. It is true that the mixture ratio of the mixed gas components remains constant. However, once the mixing ratio is adjusted, it can be changed only by a complicated connection of further or larger measuring tanks, for example, steel cylinders, to the common line upstream of the pressure-reducing valve. The mixing range is limited by the size and number of the available measuring tanks of the same pressure (German Pat. No. 458,125).

In another known device for mixing gas components, two or more pressurized gases to be mixed with each other are directed, through pressure regulators, flow-volume regulators, and adjustable regulating valves for adjusting the mixture ratio of the gas components, into a common mixing chamber. In order to maintain equal pressures in the component lines, pressure control valves are mounted downstream of the regulating valves, which are controlled, through control lines, by the static pressure in the component lines between the pressure regulators and the regulating valves. A check valve is provided between each pressure control valve in the respective component line and the mixing chamber. A mixing line comprising a control valve leads to a gas mixture storage tank from the mixing chamber. The control valve is controlled by a pressure control device which is connected to the gas mixture storage tank. Between the pressure regulators adjusted to output pressure and mounted downstream of the pressurized tanks, and the flow-volume regulators, further pressure control devices are provided by which, upon pressure drop or supply failure in one of the gas components, the mixing device is switched off. The drawback of this mixing device is that, with the pressure control valves controlled by the pressure in the component lines upstream of the regulating valves, unequal pressures may be produced in the component lines. With unequal pressures upstream of the regulating valves, it is not possible, in view of the performance characteristic of the pressure control valves and the regulating valves, to maintain a constant pressure of the desired gas mixture. Such a constant pressure, however, is absolutely necessary, for example, if the device is used in connection with respiratory or narcosis apparatus where the pressure ranges in every breathing cycle will, in practice, extend from zero to a maximum (German Utility Model No. 7,000,645).

SUMMARY OF THE INVENTION

The present invention is directed to a gas mixing device for breath-protecting, diving, medical and laboratory techniques, by which, with a control from the receiving side, the gas mixture as adjusted is delivered in any operational phase, even at varying back pressures and removed volumes.

To this end, in accordance with the invention, two or several component lines are united, downstream of the regulating valves, to a common gas mixture line in which a constant pressure is maintained by means of an admission-pressure regulator, and the pressure regulators comprise a common control line through which they are controlled by the pressures which are present in the gas mixture line downstream of the admission-pressure regulator and upstream of the pressure regulators. The pressure regulators and the admission-pressure regulator have as steep a pressure control characteristic as possible.

The advantages obtained by the invention are, in particular, the fact that, with the constant output pressure of the pressure regulators and the constant input pressure of the admission-pressure regulator, the same pressure difference is always applied to the regulating valves at the same pressure value so that the same concentration of the gas mixture is ensured. The pressure values are the same since both the pressure regulators and the admission-pressure regulator have a steep pressure regulation characteristic. This makes it possible to adjust and maintain the desired gas mixture in a simple manner, even if the proportions of the components are largely different. Due to the constant pressure in the common gas mixture line, a varying back pressure at the removal side does not affect the gas mixture. The gas mixture remains continuously constant also if:

1. the removed volume varies and even drops to zero, or
2. one of the gas components is no longer available in a satisfactory amount.

In the first case, if the removal is too small, the pressure after the admission-pressure regulator increases to a value at which the pressure regulators are closed through the common control line. In the second case, at too small a pressure in one of the component lines, the pressure regulators close. The common control line ensures that the pressure regulators close at the same instant, so that even shortly prior to a supply exhaustion, no change in the gas mixture can occur.

In a development of the invention, the common gas mixture line is provided with a storage tank equipped with a pressure switch which is controlled by the pressure in the tank. With this design, a buffer is connected before the point of removal, and provides an additional security for an accurate gas mixture.

According to a further development of the invention, pressure switches are mounted in the component lines upstream of the pressure regulators and operationally series-connected, through an on-off valve, to the common control line. The common control line may additionally be connected to the admission-pressure regulator. With the corresponding values supplied from the pressure switches, the on-off switch closes or opens the pressure regulators in the component lines and, if the additional connection is provided, the admission-pressure regulator as well. This design is simple, secure in operation and easy to maintain under surveillance.

With a simple control pressure supply, the common control line is connected to the gas mixture line and is equipped with a pressure regulator. The small amount of gas to be withdrawn from the common gas mixture line is unimportant, while the simple instrumentation of the control pressure supply for the control line is a very important factor.

Accordingly, it is an object of the invention to provide a method of supplying a mixture of gases to devices such as breath-protection, diving, medical and laboratory gas operating devices, using pressure regulators in the supply lines of each of the gases and a pressure regulator in a gas mixture line which is connected to each of the supply lines, comprising regulating the admission-pressure in the mixing line while regulating the pressures in each of the supply lines connected to the mixing line, and controlling the regulation of the pressure of the gases in the supply line by a control pressure which is regulated by a control which is actuated both by the pressure of the gases in the supply lines and the pressure of the mixed gases in the gas mixture line downstream of the admission-pressure gas regulator.

A further object of the invention is to provide a device for regulating the supply of individual gases to a mixture gas line which comprises a connection between each of the gas supply lines to the gas mixture line and a pressure regulator in each gas line which has a pressure control operated by a control gas and with a constant admission-pressure regulator in the gas mixture line and wherein the control pressure is supplied to the pressure regulators and each of the gas lines from the pressure of each gas line and also from the pressure of the mixture line downstream of the admission gas pressure regulator in this line.

Another object of the invention is to provide a gas mixture regulating device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there are illustrated preferred embodiments of the invention.

DESCRIPTION OF THE PREFERRED EMBODIMENTS

Figure 1:
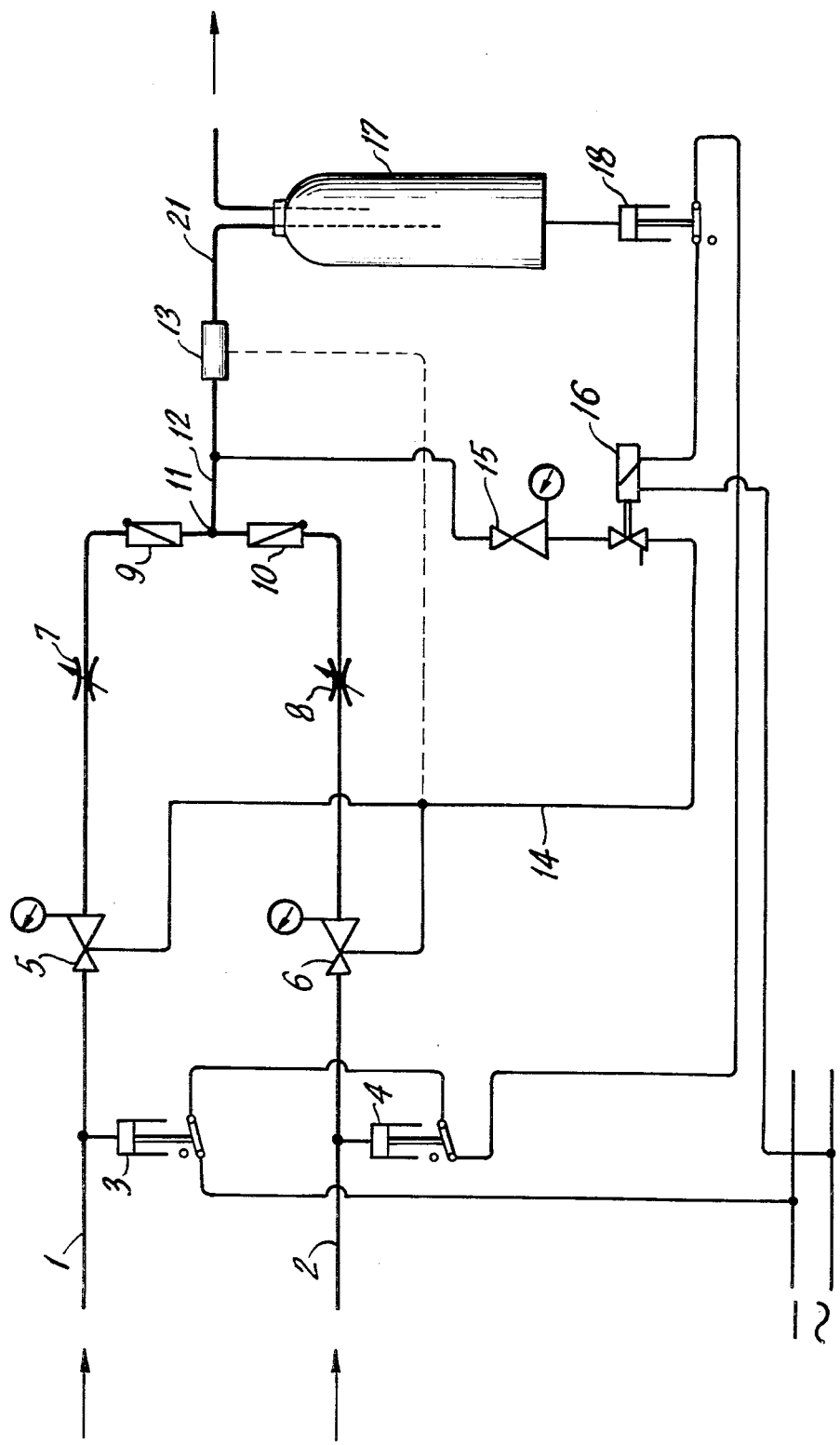
FIG. 1 is a schematic representation of a gas mixing device for mixing two gas components.

Referring to the drawings in particular, the invention embodied therein, comprises a gas mixing device for a plurality of gases which are to be mixed and which, in the embodiment shown, comprises two gas supply lines of the gases to be mixed, designated 1 and 2. Pressure regulators 5 and 6 are located in the respective lines 1 and 2, and they are adjusted to equal and constant output pressures. Regulating valves 7 and 8 are provided for adjusting the mixing ratio, and the two supply lines 1 and 2 unite at a juncture 11 in a common gas mixture line 12 which has an extension 21 downstream of a pressure regulator 13 which leads to the point of consumption.

In accordance with the invention, the gas mixture line 12 is provided with an admission-pressure regulator 13 by which the gas pressure in the component lines 1 and 2 downstream of regulating valves 7 and 8 is kept equal and constant. After admission-pressure regulator 13, gas mixture line 21 is enlarged to a mixing section which is designed as a storage tank 17. Upstream of their junction 11, each component line 1 and 2 is equipped with a check valve 9 and 10, respectively.

A common control line 14 connects the switching mechanisms of pressure regulators 5 and 6 to a control pressure source. In the present example, the common gas mixture line 12 which is kept at a constant pressure by admission-pressure regulator 13 serves as a common pressure source, but other means may be provided. The control pressure, however, is brought to a level suitable for the switching mechanism of pressure regulators 5 and 6 in a pressure regulator 15. This control pressure, in turn, is regulated by an on-off valve 16 which is actuated both by a pressure switch 18 which is actuated by the pressure in a storage tank 17, or a pressure switch 3, 4 which is actuated by the pressure in the gas supply lines 1 and 2.

By maintaining an equal pressure difference at the same pressure value, regulating valves 7 and 8 ensure a constant rate of flow of the component gases corresponding to the adjusted mixture. This is because the pressures, namely, the output pressure of pressure regulators 5 and 6, and the input pressure of admission-pressure regulator 13, are kept constant. Should the output pressure of admission-pressure regulator 13 change in a manner such that admission-pressure regulator 13 can no longer perform its controlling function, i.e., it no longer keeps the input pressure constant, then pressure switch 18 switches over so that the pressure regulators 5 and 6 are closed by the on-off valve 16.

Pressure regulators 5 and 6 are also switched off by pressure switches 3 and 4 and through the on-off valve 16 in cases where the pressure in component lines 1 and 2 drops below a minimum input pressure at which the pressure regulators 5 and 6 still keep their output pressure. This may happen, for example, if the gas components are supplied from a pressure gas cylinder and the content of the cylinder is almost exhausted.

Figure 2:
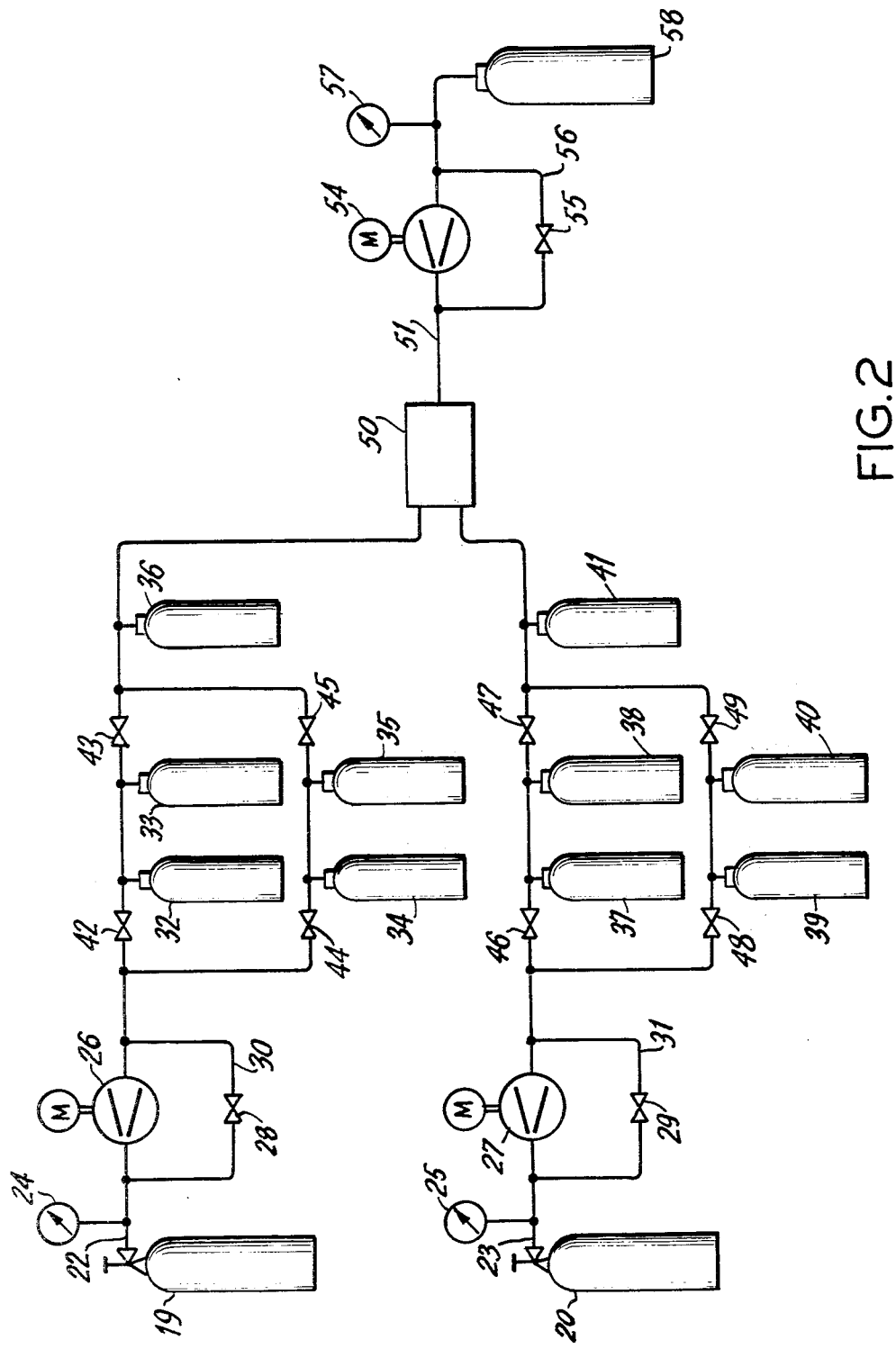
FIG. 2 is a view similar to FIG. 1 indicating the storage system for the individual gases.

In the arrangement shown in FIG. 2, the gas mixing device 50 is provided which is connected in a high pressure gas mixing plant for two gases to be mixed. In the indicated embodiment, the mixed gas is filled into high pressure cylinders 58 which are then used as supply sources for respirators. The gas components to be mixed flow from two supply cylinders 19 and 20 through supply lines 22, 23, 30 and 31, with connected storage cylinders 32, 33, 34, 35, 36, 37, 38, 39, 40 and 41, to the gas mixing device 50. From this device 50, the gas mixture is directed through a line 51 into high pressure cylinder 58. Compressors 26 and 27 in supply lines 22 and 23 make it possible to fill storage cylinders 32, 33, 37 and 38 even if the pressure in supply cylinders 19 and 20 drops below a minimum. This permits an optimum utilization of the content of supply cylinders 19 and 20. A compressor 54 connected in line 51 can be used for increasing the gas pressure of the mixture in high pressure cylinder 58 to a desired value, for example, of 200 or 300 bar. By means of valves 28, 29 and 55, bypass lines 30, 31, and 56 are closed or opened during periods of time when compressors 26, 27 and 54 are switched either on or off.

Compressors 26 and 27 make it possible to pump gas components into storage batteries formed by storage cylinders 34, 35 or 39, 40, while the gas for the mixing process is supplied from storage cylinders 32, 33 or 37, 38. The switching of the storage batteries is effected through valves 42, 43, 44, 45, 46, 47, 48 and 49. The pressure in supply cylinders 19 and 20 and in high pressure cylinder 58 is indicated in the pressure gauges 24, 25 and 57.

While specific embodiments of the invention have been shown and described in detail to illustrate the application of the principles of the invention, it will be understood that the invention may be embodied otherwise without departing from such principles.

What is claimed is:

1. A gas mixing device, comprising a plurality of gas lines for the conveyance of separate gases to be mixed, a pressure regulator in each of said gas lines having a pressure control operated by control gas to regulate the individual gas pressures in said gas lines, a common gas mixture line connected to each of said gas lines downstream of said pressure regulators, constant admission-pressure regulator means in said gas mixture line for regulating the gas mixture pressure so that it is constant in said common gas mixture line upstream of said constant admission-pressure regulator means, a control pressure connection to each of said pressure regulator pressure controls, a single control means in said control pressure connection having a control circuit connected to said common gas mixture line downstream of said constant admission-pressure regulator means for regulating the control pressure of said pressure control in each of said pressure regulators, said control pressure connection being connected to said gas mixture line upstream of said admission-pressure regulator means, said control means comprising an on-off valve in said control pressure connection controlled by said control circuit, whereby the control pressure is not varied by changes in the amount of gas supplied by said admission pressure regulator means unless said admission-pressure regulator means can no longer maintain constant pressure in said common gas mixture line upstream of said admission-pressure regulator means.

2. A gas mixing device, according to claim 1, wherein said pressure regulators and said constant admission-pressure regulator means have a narrow pressure control characteristic.

3. A gas mixing device, according to claim 1, including a storage vessel in said common gas mixture line, said control means control circuit comprising a pressure switch controlled by pressure in said storage vessel.

4. A gas mixing device, according to claim 1, which further includes a pressure switch connected in each of said gas supply lines upstream of said pressure regulators.

5. A gas mixing device, according to claim 1, which further includes a pressure control switch in each of said gas lines and a pressure control switch in said gas mixture line, said on-off valve actuated by each of said pressure switches.

6. A gas mixing device, according to claim 5, wherein said pressure switches are arranged in series.

7. A method according to claim 1, wherein the gases in the gas mixture line are expanded into an expansion tank downstream of the constant pressure regulator.

8. A method of supplying a mixture of gases to breath-protecting, diving, medical and laboratory devices, using pressure regulators in the supply lines of each of the gases and a pressure regulator in a gas mixture line which pressure regulator is connected to each of the supply lines, comprising, regulating the admission-pressure in the mixing line while regulating the pressure in each of the supply line connections to the mixing line, and controlling the regulation of the pressures of the gases in the supply lines by regulating them in accordance with the pressures of the gases in the respective supply lines and the pressure of the mixed gases in the gas mixture line upstream of the admission-pressure regulator, the gas pressure for controlling the pressure in the supply lines being tapped from the gas mixture line and regulated by an on-off valve in accordance with the pressure conditions in the supply lines and the gas mixture line.

* * * * *